United States Patent [19]

Pittman, Jr.

[11] 4,302,452

[45] Nov. 24, 1981

[54] USE OF DERIVATIVES OF 6α-METHYLPREDNISOLONE AS AN ANTIEMETIC

[75] Inventor: Johnny M. Pittman, Jr., Memphis, Tenn.

[73] Assignee: The Upjohn Company, Kalamazoo, Mich.

[21] Appl. No.: 209,078

[22] Filed: Nov. 21, 1980

Related U.S. Application Data

[62] Division of Ser. No. 144,000, Apr. 25, 1980, abandoned.

[51] Int. Cl.$^3$ .............................................. A61K 31/56
[52] U.S. Cl. ..................................................... 424/243
[58] Field of Search ........................................ 424/243

[56] References Cited

U.S. PATENT DOCUMENTS 2,897,218  7/1959  Sebek et al. .................... 260/397.45

*Primary Examiner*—Elbert L. Roberts
*Attorney, Agent, or Firm*—Sidney B. Williams, Jr.

[57] ABSTRACT

Use of water soluble 21-polybasic esters of 1-dehydro-6α-methylhydrocortisone and their salts as an antiemetic.

4 Claims, No Drawings

USE OF DERIVATIVES OF 6α-METHYLPREDNISOLONE AS AN ANTIEMETIC

This is a division of application Ser. No. 144,000, filed Apr. 25, 1980 now abandoned.

DESCRIPTION

BACKGROUND OF THE INVENTION

1. Field of the Invention

This invention relates to a method of using water soluble 21-polybasic esters of 1-dehydro-6α-methylhydrocortisone and their salts for the prevention of nausea and vomiting caused by chemotherapy. One of the most incapacitating problems in the administration of chemotherapeutics in the treatment of cancer is the nausea and vomiting caused thereby. These conditions are most pronounced in cases where the drug is administered intravenously. The nausea and vomiting is, in general, experienced from one-half to forty-eight hours after administration of the chemotherapeutic. This condition also seems to be more severe with the use of the newer and more effective chemotherapeutics; for example, Adriamycin and Cis-Platinum.

2. Description of the Prior Art

1-Dehydro-6α-methylhydrocortisone (6α-methylprednisolone) is a known pharmaceutical for treating inflammation. It has the following formula:

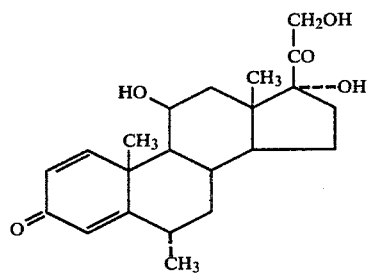

Water soluble 21-polybasic esters of 1-dehydro-6α-methylhydrocortisone, their salts and methods for preparing them are described in U.S. Pat. No. 2,897,218.

Pittermann et al., *Wiener Medizinische Wochenschrift*, No. 14/1974, pp. 216–221, discloses that Prednisolone can be used to control nausea and vomiting resulting from the use of Peptichemio in chemotherapy. Also, the instant Applicant is aware that Dexamethasone has been used to prevent nausea and vomiting in chemotherapy. Other antiemetics have been used in efforts to prevent nausea and vomiting resulting from chemotherapy. They include Compazine, Tigan and Thorazine. Many of these antiemetics have the side effect of narcotizing the patient to such a degree that they suffer hangovers that last for up to a week. Insofar as Applicant knows, water soluble 21-dibasic esters of 1-dehydro-6α-methylhydrocortisone and their salts have never been used as an aid to prevent nausea and vomiting in chemotherapy.

SUMMARY OF THE INVENTION

The method of this invention comprises treating patients undergoing chemotherapy with water soluble 21-dibasic esters of 1-dehydro-6α-methylhydrocortisone and their salts in an amount that is equivalent to from 0.250 to 3 grams of 1-dehydro-6α-methylhydrocortisone on the day in which chemotherapy is undertaken. This method is especially useful for treating patients that are being administered the chemotherapeutic agent Cis-Platinum.

DETAILED DESCRIPTION OF THE INVENTION

In accordance with the manner and process of using the present invention, water soluble 21-dibasic esters of 1-dehydro-6α-methylhydrocortisone and their salts are administered intravenously to mammals and animals to prevent chemotherapeutic-induced nausea. An especially effective compund for use in the process of this invention is 1-dehydro-6α-methylhydrocortisone 21-hemisuccinate sodium salt (6α-methylprednisolone 21-succinate sodium salt).

The water soluble 21-dibasic esters of 1-dehydro-6α-methylhydrocortisone and their salts can be prepared by methods known in the art. U.S. Pat. No. 2,897,218 discloses such a method. The essential material constituting a disclosure of how to prepare and formulate said esters and salts is incorporated here by reference from U.S. Pat. No. 2,897,218.

The water soluble 21-dibasic esters of 1-dehydro-6α-methylhydrocortisone and their salts can be formulated for use in sterile intravenous solutions by methods that are conventional in the art.

The formulation as prepared can be administered in varying dosages depending upon the weight of the mammal under treatment. In the case of humans the daily dosage ranges from 0.250 to 3 grams. The preferred regimen of administration when Cis-Platinum is used as the chemotherapeutic agent is five equal doses. The first dose should be administered about one-half to one-and-a-half hours prior to beginning chemotherapy; the second dose 2 to 4 hours after chemotherapy and the last three doses at 6 to 8 hour intervals.

The following Example is illustrative of the method of this invention, butis not to be construed as limiting.

EXAMPLE 1

Enough formulation containing 1-dehydro-6α-methylhydrocortisone 21-hemisuccinate sodium salt, as the active ingredient, to prepare 1000 8 ml vials, each containing the equivalent of 500 mg of methylprednisolone is prepared from the following types and amounts of ingredients.

| | |
|---|---|
| 1-Dehydro-6α-methylhydrocortisone 21-hemisuccinate sodium salt (equivalent to 500 mg/vial of 1-dehydro-6-α-methyl-hydrocortisone itself) | 663 grams |
| Sodium Biophosphate, Anhydrous | 6.4 grams |
| Dried Sodium Phosphate | 69.6 grams |
| Benzyl Alcohol | 66.8 grams |

Sterile intravenous solutions of the prepared formulations can be prepared by mixing the content of a vial with 8 ml of bacteriostatic water.

The sterile solution is administered as follows, to prevent chemotherapy-induced nausea and vomiting. One vial one-half hour before chemotherapy is started. If Cis-Platinum is the chemotherapeutic agent, another vial is given 4 hours after chemotherapy has been stopped and three subsequent vials given at six hour intervals.

Other 21-polybasic esters of 1-dehydro-6α-methylhydrocortisone and their salts can be used to prepare formulations that can be used in the method of this invention. They include:

- 1-dehydro-6α-methylhydrocortisone 21-hemisuccinate phenylephrine salt
- 1-dehydro-6α-methylhydrocortisone 21-hemisuccinate N-methyl-glucamin salt
- 1-dehydro-6α-methylhydrocortisone 21-(α,β-dimethylglutamate)
- 1-dehydro-6α-methylhydrocortisone 21-glycolate
- 1-dehydro-6α-methylhydrocortisone 21-tartrate and the sodium phenylephrine and N-methyl-glucamin salts thereof.

I claim:

1. A method for the prevention of chemotherapeutic-induced nausea and vomiting which comprises administering intravenously to a patient expecting chemotherapy, a formulation comprising a compound selected from the group consisting of water soluble 21-dibasic esters of 1-dehydro-6α-methylhydrocortisone and their salts and a pharmaceutically-acceptable carrier.

2. A method according to claim 1 wherein the compound is 1-dehydro-6α-methylhydrocortisone 21-hemisuccinate sodium salt.

3. A method according to claim 1 or 2 wherein the amount of compound administered is equivalent to 0.250 to 3 grams of 1-dehydro-6α-methylhydrocortisone.

4. A method according to claim 1 or 2 wherein the chemotherapeutic agent inducing the nausea and vomiting is Cis-Platinum and wherein the formulation is administered both prior to and subsequent to the administration of the chemotherapeutic agent.

* * * * *